United States Patent [19]

Willis, Jr. et al.

[11]  4,355,181
[45]  Oct. 19, 1982

[54] PROCESS FOR ETHANOLAMINES

[75] Inventors: Stephen B. Willis, Jr.; Joseph D. Henry, both of Lake Jackson, Tex.

[73] Assignee: The Dow Chemical Company, Midland, Mich.

[21] Appl. No.: 238,894

[22] Filed: Feb. 27, 1981

[51] Int. Cl.³ .................... C07C 89/02; C07C 85/04
[52] U.S. Cl. .................................. 564/477; 564/475; 564/476
[58] Field of Search ................... 564/475, 477, 476

[56]  References Cited

U.S. PATENT DOCUMENTS

| 2,051,486 | 8/1936  | Kautter    | 564/477   |
| 2,586,767 | 2/1952  | Wilson     | 564/475 X |
| 3,131,132 | 4/1964  | Moss et al.| 564/475 X |
| 3,639,403 | 2/1972  | Muhlbauer  | 564/477 X |
| 3,849,262 | 11/1974 | Cocuzza    | 564/475 X |
| 4,119,670 | 10/1978 | Tsuchiya   | 564/477   |
| 4,169,856 | 10/1979 | Cocuzza et al. | 564/477 |

FOREIGN PATENT DOCUMENTS

| 540963  | 5/1957 | Canada              | 564/477 |
| 1543641 | 7/1969 | Fed. Rep. of Germany| 564/475 |
| 7312683 | 3/1974 | Netherlands         | 564/477 |

*Primary Examiner*—John Doll
*Attorney, Agent, or Firm*—A. Cooper Ancona

[57]  ABSTRACT

In a process of making ethanolamines by reacting ethylene and ammonia and wherein ammonia is used in excess of the stoichiometric amount, the improvement comprising flashing and liquification at least part of the excess ammonia in the effluent prior to recycling. This moderates the operating conditions and simplifies the equipment needed to recycle the balance of the ammonia.

4 Claims, 1 Drawing Figure

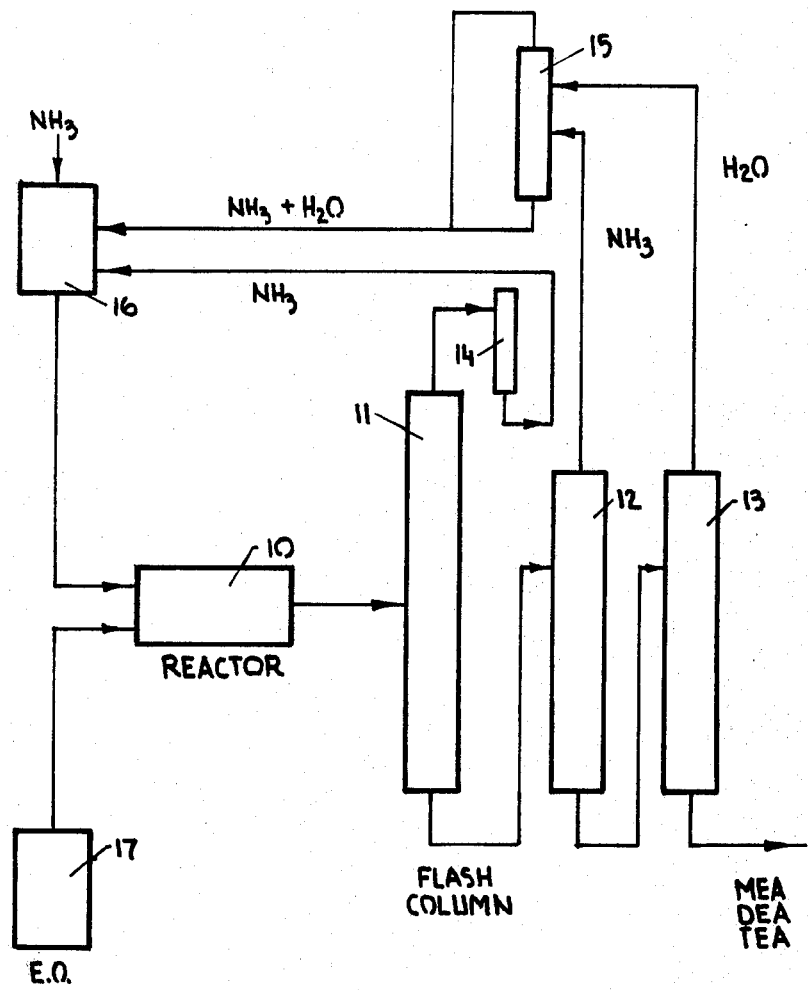

PROCESS FOR ETHANOLAMINES

BACKGROUND OF THE INVENTION

This invention relates to an improved process for preparing ethanolamines by reacting ethylene oxide with ammonia. From another viewpoint, the invention relates to a process for effectively recovering the unreacted ammonia in the reaction of ethylene oxide (EO) with ammonia ($NH_3$).

Ethanolamines find a wide range of applicants as detergents, emulsifiers, gas absorbents, corrosion inhibitors, gloss-imparting agents, polishes, textile treating assistants, and raw materials for herbicides, pharmaceuticals, etc.

They can be produced by the reaction of ethylene halohydrins or ethylene oxide with ammonia, but the current commercial-scale production of ethanolamines almost entirely relies on the reaction of ethylene oxide with ammonia.

The reaction of ethylene oxide addition to ammonia not only yields monoethanolamine (MEA), but also diethanolamine (DEA) and triethanolamine (TEA). The ratios of the ethanolamines in the reaction product is determined by the mol ratio of ammonia to ethylene oxide. For example, to obtain a reaction product containing a major proportion of MEA, a large excess of ammonia should be reacted with ethylene oxide. This procedure requires a heating source, for example a large quantity of steam, to recover the excess of ammonia after the reaction.

The addition reaction between ethylene oxide and ammonia is an exothermic reaction. In known processes using reactors with shell and tubes, it is the common practice to cool the outside of a reaction zone with cooling water, etc. so as to restrict the reaction temperature to 50° to 150° C. It is also known to react ethylene oxide and ammonia adiabatically, and desorb the ammonia by releasing the elevated pressure. Since the inside of the reactor attains high temperatures and pressures, a large-scale apparatus is required, and the resulting ethanolamines, especially TEA, tend to be colored. In this process, the equipment needed becomes larger, the larger the ratio of $NH_3/EO$. Water is employed both as a catalyst and an absorbent in the reaction, the latter facilitating recycle of the excess ammonia.

The present improved process, by employing a high pressure flash distillation and liquification of part of the $NH_3$ avoids the need for ever larger absorbers or compressors as the ratio of $NH_3/EO$ increases. This also reduces the severity of the process conditions necessary to recycle the ammonia when the ratio of $H_2O/NH_3$ fed to the reactor is limited (reduced) for economic reasons. The direct liquefaction of $NH_3$ is also a convenient and economical method to prepare $NH_3$ for recycle in the anhydrous reaction of $NH_3$ and EO.

SUMMARY OF THE INVENTION

An improved process for making ethanolamines by the reaction of ethylene oxide and ammonia wherein at least a part of the excess ammonia from the reaction is flashed and condensed, while the remaining excess ammonia is absorbed in water or liquified by compression and/or refrigeration prior to being recycled to the reactor. This improvement allows the size of the ammonia absorber and stripper to become essentially independent of the $NH_3/EO$ ratio as well as reduces the size of compressors or refrigeration units needed or eliminates them entirely.

DETAILED DESCRIPTION OF THE INVENTION

The process of the present invention is adaptable to any process in which a relatively volatile reactant must be used in significant excess in order to control the product distribution from the reaction. The use of the invention is especially indicated if the reactant is customarily prepared for recycle by absorption into a liquid such as water since the amount of the absorbing liquid should be minimized for economic reasons. Attempts to achieve economically desirable levels of absorbing liquid often lead to excess pressures and resulting high temperatures in the bottom of the stripping column or to the addition of compressors and/or refrigeration units. Such high temperatures are undesirable because they often result in products of inferior quality, while the addition of more equipment has obvious disadvantages.

The invention is illustrated in the process of making ethanolamines by reacting ammonia and ethylene oxide. The product is a mixture of monoethanolamine together with lesser amounts of di- and triethanolamines. An excess of ammonia favors the formation of the monoethanolamine. The excess ammonia which does not react is customarily absorbed into water and recycled to the process. The concentration of the ammonia/water solution is a function of the temperature of the water and the ammonia pressure in the absorber. It is economically desirable to limit the amount of water fed to the reactor since this water must be later separated from the products of the reaction. This separation requires either considerable energy or the addition of expensive equipment such as multiple effect evaporators to minimize this energy use. The present invention involves an improvement which limits the amount of energy and equipment associated with the recycling of the excess ammonia. A high pressure flash is employed immediately following the reactor where a portion of the ammonia that is not reacted is flashed overhead leaving the reaction product amines as the bottoms. The remaining ammonia left dissolved in the ethanolamines product is distilled off at a lower pressure in a first distillation column and water is removed from the product in a second distillation column. The ammonia from the high pressure flash is directly condensed and sent to a makeup or holding tank while that removed as the overhead in the first distillation is sent to a water absorber unit. The water removed from the amines product is sent to the water absorber unit. The aqueous ammonia from the absorber unit is sent to the makeup or holding tank and from there recycled to the reactor as 85–90% ammonia, there being enough water present to act as catalyst for the reaction.

A representative process is described in connection with the drawing.

Thus, ethylene oxide from tank 17 and ammonia from tank 16 are introduced into a reactor 10, together with sufficient water to catalyze the reaction, at a mol ratio of about 5 mols $NH_3$ per mol of EO. The effluent product is sent to flash column 11, operated at a pressure of ~300 psig. Ammonia is taken overhead and sent to a condenser 14 and thence to makeup tank 16. The remaining ammonia, water and mixture of ethanolamines is taken off the bottom of column 11 and introduced into distillation column 12 operated at about 30 psig and at a temperature of about 140° C. Ammonia is taken overhead and sent to absorber 15 where it is absorbed in water. The water and amines are taken off the bottom of column 12 and sent to a second distillation column 13 operated under reduced pressure. Water is taken overhead and sent to absorber 15. Amines are taken out of the bottom of column 13 and sent to separation columns (not shown) where the mono-, di- and trithanolamines are recovered. The $NH_3$ from condenser 14 and aqueous $NH_3$ from absorber 15 are conveniently sent to tank 16 and thence to reactor 10.

The mol ratio of $NH_3$ to EO can be from about 3/1 to about 40/1 depending upon the desired product mix. The reactor 10 is operated at a temperature of from about 50° to about 175° C. and preferably from about 100° to about 130° C. Water employed as the catalyst is generally present at about 0.1 mol per mol of $NH_3$ but may be as high as 1 or as low as 0.05. The pressure in the ammonia flash column 11 is generally from about 220 to about 350 psig, but preferably 280 to 310 psig.

Column 12 for removing the remaining ammonia from the flash column 11 bottoms is generally operated at about 30 psig, but may be operated at from 15 to about 70 psig. It is preferably operated at a pressure such that the temperature of the amines and water in the bottom of column 12 does not exceed about 150° C.

Generally 70-85% of the total excess ammonia is removed in the high pressure flash. It is desirable to remove at least 50% but probably no more than about 90-95% of the excess $NH_3$. The % of the excess ammonia removed in the high pressure flash depends on the amount of water desired to promote the reaction. In the case in which 0.1 mol of $H_2O$ per mol of $NH_3$ is used, approximately 90% of the $NH_3$ would be conveniently removed in the high pressure flash. This would allow the absorber to run at relatively mild conditions while the $NH_3/H_2O$ solution fed to the reactor would be about 90% $NH_3$. Operating at about 90% $NH_3$ in the feed under the conditions of the prior art without the high pressure flash would require excessively high temperatures during distillation, e.g. in column 12, which are deleterious to the products, producing color and by-products.

The advantages of this improved process are that less energy is required since a portion of the ammonia is removed in the high pressure flash without being absorbed in water. At the same time, since less ammonia is removed at low pressures, as in the known process, a lower temperature is employed which permits a purer amine product to be obtained and reduces the corrosion problems in the aqueous ammonia recycle system.

Another advantage is that less capital is required for equipment since smaller volumes of water must be recycled. The plant would be easier to operate as the liquid ammonia recycle system would absorb swings in $NH_3$/EO mol ratio, leaving the aqueous ammonia recycle section of the plant with a constant feed of water and ammonia.

We claim:

1. In a process for making alkanolamines by the reaction of an alkylene oxide and ammonia in the liquid phase, said ammonia being employed in stoichiometric excess and in which said excess is recovered from the reaction product and recycled to said reaction, the improvement which comprises (1) reacting said ammonia and said alkylene oxide in the presence of from about 0.05 mol to about 1.0 mol of water per mol of ammonia, (2) removing the reaction product from the reactor and flashing a portion of the ammonia in a distillation column under a pressure of from about 220 to about 350 psig, (3) condensing said portion of ammonia, (4) sending the remaining reaction product and remaining ammonia to a low pressure distillation column to remove said remaining ammonia overhead, (5) sending the bottoms of step 4 comprising water and alkanolamines to a reduced pressure distillation to remove said water, (6) sending said water to an ammonia absorber unit, (7) sending said ammonia removed overhead in step 4 to said absorber unit, (8) recycling said condensed ammonia from step 3, said absorbed ammonia from step 6 and said water removed in step 5 to said reaction.

2. The process of claim 1 wherein the pressure in step (4) is maintained at a pressure such that the bottoms temperature of said distillation does not exceed about 150° C.

3. The process of claim 1 wherein at least 30% of the excess ammonia is removed in step (2).

4. The process of claim 1 wherein the ratio of $NH_3$ to EO is from about 3/1 to about 40/1, the pressure employed in steps 2 and 3 is about 280-310 psig and the temperature in step 2 is maintained so as to give a mol ratio of $NH_3$ to $H_2O$ of from about 1.2/1 to 0.12/1 in the feed to step 4.

* * * * *